United States Patent [19]

Kuljis et al.

[11] Patent Number: 4,509,369
[45] Date of Patent: Apr. 9, 1985

[54] NEAR SURFACE INSPECTION SYSTEM

[75] Inventors: Zoran Kuljis, Zagreb, Yugoslavia; John P. Lareau, Granby, Conn.

[73] Assignee: Combustion Engineering, Inc., Windsor, Conn.

[21] Appl. No.: 526,187

[22] Filed: Aug. 25, 1983

[51] Int. Cl.³ ............................................ G01N 29/04
[52] U.S. Cl. .................................... 73/628; 73/627; 376/249
[58] Field of Search ................ 73/628, 641, 625, 620, 73/624, 627, 598; 376/249, 252

[56] References Cited

U.S. PATENT DOCUMENTS

| | | | |
|---|---|---|---|
| 3,683,680 | 8/1972 | Johnson et al. | 73/628 |
| 3,739,628 | 6/1973 | Saglio | 73/627 |
| 3,813,926 | 6/1974 | Stubbeman | 73/627 |
| 4,165,649 | 8/1979 | Greer, Jr. | 73/627 |

Primary Examiner—Stephen A. Kreitman
Attorney, Agent, or Firm—Troxell K. Snyder

[57] ABSTRACT

An ultrasonic transmitter (10) and at least two ultrasonic receivers (12, 16) are mounted on a carrier (18) which traverses the surface (22) of a solid material (24). The sound beam (30) from the transmitter (10) passes beneath the surface (22) and enters a zone of interest disposed about a point (36) located a fixed distance (40) beneath the surface (22). Reflected sound beams (42, 46) emanating from flaws (54, 58, 60) located within the zone of interest are detected by the receivers (12, 16). The orientation and positioning of the transmitter (10) and the receivers (12, 16) for maximizing the detection and differentiation of the detected flaws (54, 58, 60) are also disclosed.

11 Claims, 6 Drawing Figures

NEAR SURFACE INSPECTION SYSTEM

FIELD OF THE INVENTION

The present invention relates to a method and an apparatus for inspecting a solid material for internal flaws, and more particularly, to a method and an apparatus for ultrasonically inspecting a solid material for internal flaws located near the surface of said material.

BACKGROUND OF THE INVENTION

Nondestructive methods of evaluation have long been used to examine the interior portions of solid bodies for the detection of flaws or other defects. One such method in wide use today is that of ultrasonic testing.

In this method an ultrasonic transmitter is used to send a beam of sound energy beneath the surface of the solid body. Should this ultrasonic sound beam encounter any defects such as a crack, an inclusion of foreign material, a gap, etc., a reflected sound wave will be created which may be detected by a receiver also positioned above the surface of the solid body. Depending on the nature of the defect, the sound beam may be reflected in a direction which does not coincide with the current position of the receiver. For this reason, it is often necessary to perform multiple traverses of the surface of the body being inspected in order to insure that all internal flaws have been detected.

Moreover, even if a flaw should be detected by the currently used method of inspection, it is often not immediately possible to determine the depth of the flaw as the reflected sound wave may originate from a variety of depths beneath the surface of the solid body. This is especially cumbersome in the case of a pressure vessel having an internal cladding bonded to a substrate of other material. In this situation, the main zone of interest is the interface between the cladding and the substrate material, with flaws occurring deep in the substrate being of less consequence to the functionality of the pressure vessel. A prior art ultrasonic inspection system could detect flaws of widely varying depth in the first traverse, thus requiring additional inspections to determine if the flaw is an inconsequential defect in the substrate, or an unacceptable defect occurring between the cladding and the substrate.

One such situation in which very stringent inspection requirements are present is that of a nuclear reactor pressure vessel having a substrate of carbon steel and an inner cladding of stainless steel ⅜ inch (1.0 cm) in thickness. A flaw occurring between the stainless steel cladding and the carbon steel substrate could eventually result in a failure of the vessel and the release of the high pressure contents of the vessel. As such vessels are typically very large, and the inspection requirements very stringent, the need for multiple traverses in differing directions and with differing receiver/transmitter orientations results in an expensive and lengthy procedure.

What is required is a method and an apparatus for inspecting the zone of interest between the cladding and the substrate in a large pressure vessel which does not require multiple traverses to determine the existence of a flaw, and which is not susceptible to the detection of inconsequential flaws occurring in the substrate out of the zone of interest.

SUMMARY OF THE INVENTION

The present invention provides an ultrasonic inspection system which makes possible the complete inspection of a zone of interest near the surface of a solid material with just one traverse by the inspection equipment. The system uses one ultrasonic transmitter and preferably two ultrasonic receivers which are arranged so as to provide maximum sound strength and sensitivity within the zone of interest.

The transmitter is secured to a carrier which traverses the surface of the solid body to be inspected at a fixed spacing. The transmitter is oriented so as to send a beam of ultrasonic sound through a conducting medium and into the solid material eventually passing through the zone of interest at a preselected depth beneath the surface. The transmitter is further oriented so as to result in the included angle between the surface and the beam path within the solid being equal to approximately 20°. This angle, in addition to the transmitter being spaced from the surface so as to result in the sound beam length from the transmitter to the zone of interest being equal to the Fresnel distance for the medium and the solid, provides maximum sound intensity at the zone of interest.

Should a flaw or imperfection be present within the zone of interest, a reflected sound wave will be generated. The system, according to the present invention, detects the reflected sound by receivers secured to the carrier and angularly oriented in a manner similar to that of the transmitter with respect to the plane of the surface, thus resulting in the reception of only those sound waves emanating from within the zone of interest. In the preferred embodiment, two receivers are positioned on the carrier opposite one another and directed toward the zone of interest for receiving sound reflected laterally with respect to the transmitted sound beam. This positioning allows the system according to the present invention to be used to detect and differentiate between both circumferential and longitudinal cracks in a large cylindrical surface, such as the interior of a large nuclear pressure vessel, in only one traverse.

An alternative embodiment is also disclosed which includes a third receiver positioned on the carrier opposite the transmitter with respect to the zone of interest for receiving reflected signals traveling in the same direction in the plane of the surface as the transmitted sound beam. The third receiver is thus effective in detecting delamination between a cladding and a substrate such as may occur within a clad nuclear pressure vessel.

By positioning the transmitter and receivers as disclosed herein, the present invention restricts the detection of flaws within the solid body to a zone of interest located a predetermined depth beneath the surface of the body. Moreover, by positioning the receivers in a plurality of orientations about the zone of interest during the inspection process, the present invention permits the system operator to detect and differentiate between a variety of defects without the need for multiple traverses of a particular point,

BRIEF DESCRIPTION OF THE DRAWING FIGURES

Figure 4A:
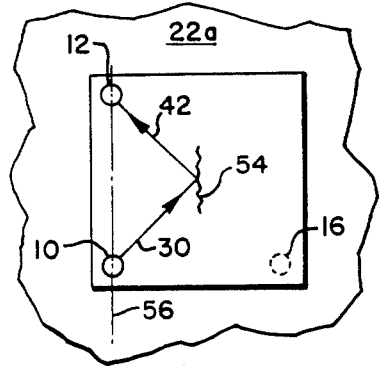
Figure 4B:
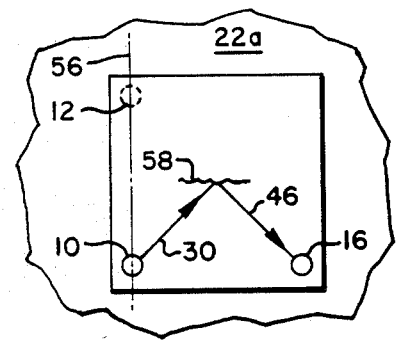
Figure 4C:
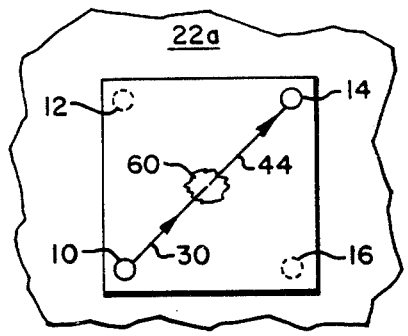

FIGS. 4a, 4b, and 4c show the effect of different types of flaws upon the direction of the reflected sound beam when viewed in the plane of the surface.

DESCRIPTION OF THE DISCLOSED EMBODIMENTS

Figure 1:
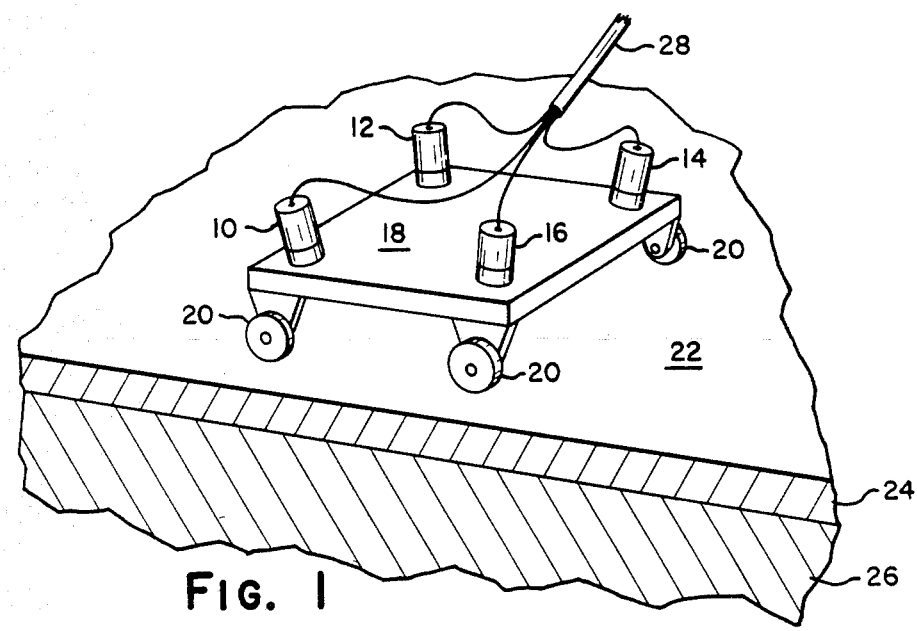
FIG. 1 shows an isometric view of the present invention in the process of traversing a surface of a solid material.

FIG. 1 discloses the preferred embodiment of the present invention having an ultrasonic transmitter 10 and two opposing ultrasonic receivers 12, 16 mounted on a movable carrier 18. Also disclosed in FIG. 1 is an alternative embodiment in which an additional receiver 14 is also secured to the carrier 18.

The carrier 18 is shown as including means 20 for maintaining the carrier at a fixed distance above the substantially planar surface 22 of the solid material being inspected. These means 20, while disclosed herein as simple wheels or castors affixed to the carrier 18 and rolling over the surface 22, may alternatively be any of a wide variety of positioning aids such as a mechanical boom (not shown) affixed rigidly at a point elsewhere on the solid body for accurately manipulating the carrier 18 over the surface 22 or any other means which might be used to position the carrier 18. The type of positioning mechanism used will depend upon the particular application and restraints under which the inspection system must operate, and are therefore disclosed here in only an illustrative, rather than a limiting sense.

The solid body of which the surface 22 is a part is shown in FIG. 1 is a composite body having a cladding 24 applied over a substrate 26. In the case of a nuclear reactor vessel, the substrate 24 would be a material such as stainless steel and have a thickness of approximately ⅜ inch (0.1 cm). The substrate 26 in this situation is usually a form of carbon steel and is considerably thicker than the stainless steel cladding 24.

When inspecting a clad vessel such as that disclosed in FIG. 1, it is of critical importance that no cracks or other flaws be present at the interface between the cladding 24 and the substrate 26 in order to avoid possibility of a failure during the operation of the nuclear reactor. Current inspection guidelines call for a complete inspection of this interface for the entire interior vessel surface in order to detect both circumferential and longitudinal cracks as well as other imperfections which may be present.

The transmitter 10 is an ultrasonic oscillator typically operating at a frequency of 2.25 megahertz. The transmitter emits a directed beam of ultrasonic energy downward beneath the surface 22 of the cladding 24 through a medium (not shown in FIG. 1) of sound conducting liquid, such as water. Sound waves reflected by flaws beneath the surface 22 travel upward leaving the surface and are detected by the receivers 12, 14, 16 which are similar to directional microphones in that their angle of best reception is limited to a specific direction. The powder for the transmitter 10 and the electrical signals representing the intensity of the detected sound waves from each of the receivers 12, 14, 16 travel from a control location (not shown) of electrical conductors 28 shown in FIG. 1 or other means. The power supply and signal interpretation apparatus are well known in the art of ultrasonic inspection and need not be described herein. Suffice to say that the interpretation apparatus operates so as to determine the existence of an abnormally high level of received sound at one of the receivers 12, 14, 16, above the normal background or interference sound level. Such an abnormally high level of sound indicates the presence of a reflective flaw beneath the surface 22.

Figure 2:
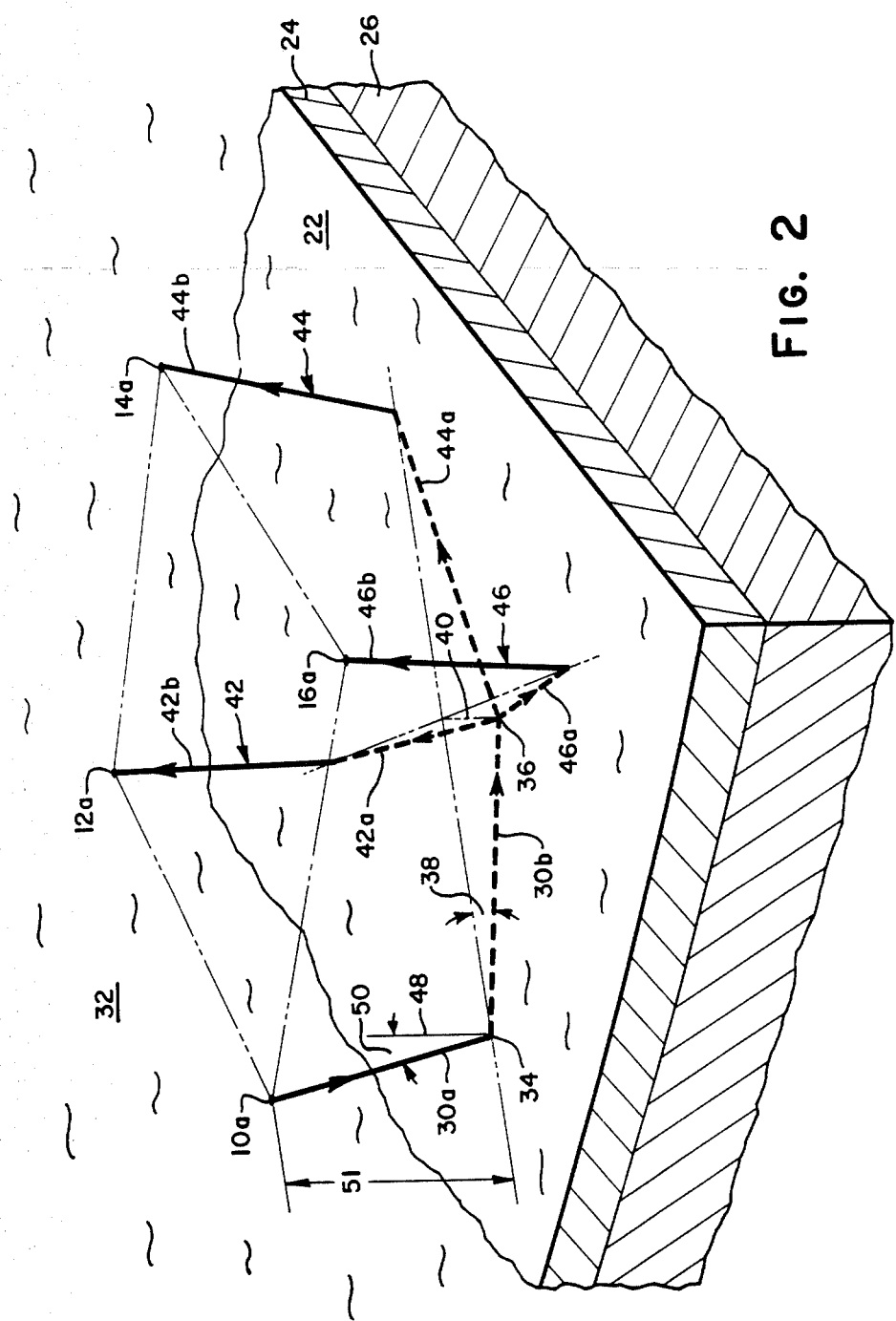
FIG. 2 shows a sketch of the angular relationship of the transmitted ultrasonic beam and the direction of the reflected beams being received by the receivers.

FIG. 2 is a schematic representation of the centerlines of the paths of the sound beams, both transmitted and reflected, as they would appear if visible. The transmitter 10 and the receivers 12, 14, 16 of FIG. 1 are represented in FIG. 2 by the points labeled 10a, 12a, 14a, and 16a, respectively. The path of the transmitted sound beam 30 is shown traveling through the conductive medium 32 (portion 30a), encountering the surface 22 of the cladding 24 at point 34, and then traveling (portion 30b) through the solid material 24 to the focal point 36 located a predetermined distance 40 beneath the surface 22 within the solid 24.

It is important to note that the sound beam 30 is refracted upon encountering the solid material 24 due to the difference between the speed of sound in the conductive medium 32 and the solid material 24. This refraction when moving through an interface between dissimilar materials causes the abrupt angle between the two portions 30a, 30b of the transmitted sound beam 30 at the surface point 34. This surface refractive phenomenon, well known for waves of sound traveling between different media, may be calculated using basic principles of acoustics.

According to the present invention, the transmitter 10 has been oriented with respect to the plane of the surface 22 so as to result in the formation of an included angle 38 between the plane of the surface 22 and the path of the transmitted sound beam 30b within the solid material. This angle of approximately 20° has been determined through experience to be the optimum angle for the transmission of the ultrasonic sound energy within the solid material 24 for the detection of flaws present at relatively shallow depths beneath the surface 22. It has been found that an angle 38 having a magnitude greater than 20° results in the transmitted beam 30b traveling deeply within the solid 24, 26, and resulting in a loss of effectiveness. An angle 38 of less than 20° results in the formation of a surface wave along the surface 22 as well as reflection from the surface back into the conducting medium 32 and certain mode conversions all of which attenuate the sound beam within the solid material 24.

The focal point 36 is located a predetermined depth beneath the surface 22 of the solid material 24. This depth, designated 40 in FIG. 2 is selected depending upon the particular application to which the inspection system is addressed. In this case of a nuclear reactor vessel having a stainless steel cladding 24 on the interior of a carbon steel substrate 26, this predetermined depth 40 would be selected to be equal to the thickness of the cladding 24, typically about ⅜ inch (1.0 cm). It is now possible to define a zone of interest about the focal point 36 in which the presence of a flaw will result in a reflected sound signal traveling in a direction dependent upon the nature of the flaw and the direction of the transmitted sound beam. This zone of interest may be considered to be a volume surrounding the focal point 36 and having a diameter dependent upon the width of the transmitted sound beam emanating from the transmitter 10. A narrower sound beam results in a correspondingly smaller zone of interest, and vice versa. For a typical ultrasonic transmitter having a one-inch (2.5 cm) diameter sound generator would result in a zone of interest surrounding the focal point 36 of about ½ inch (1.3 cm) diameter in the preferred embodiment of the present invention.

The receivers 12, 14, 16 are secured to the carrier 10 as shown in FIG. 1 and are oriented so as to receive reflected sound radiation traveling along pathways 42, 44, 46, respectively. By orienting the receivers 12, 14, 16 in this manner, unwanted reflections from flaws not within the zone of interest are excluded from reception. As can be clearly seen from the drawing figure, the reflected sound paths 42, 44, 46 are identical in shape to that of the transmitted sound path 30, varying only in direction and position. Those portions of the reflected sound paths within the solid material 24, designated as 42a, 44a and 46a thus each form angles of about 20° with the plane of the surface 22 and are also refracted as they each pass from the solid 24 into the medium 32.

It can be seen in FIG. 2 that points 10a, 12a, 14a, and 16a form a square in a plane which is parallel to the plane of the surface 22. In the preferred embodiment according to the present invention, the first receiver 12 and the second receiver 16 are placed equidistant from the transmitter 10 and positioned so as to form an isosceles right triangle with the apex located at point 10a. The alternate embodiment, wherein a third receiver 14 is added, is fully disclosed in FIGS. 1 and 2 and shows the formation of a square 10a, 12a, 14a, 16a, with the receiver 14 positioned at the corner 14a opposite that of the transmitter 10.

For a conducting medium 32 composed of water, and the cladding material 24 composed of stainless steel, the angle formed by the pathway of the portion 30a of the transmitted sound beam traveling through the medium 32 and a perpendicular rising from the plane of the surface 22 at the point of intersection 34 (the perpendicular being denoted 48) would be approximately 13.9°. As discussed hereinabove, should the composition of the conductive medium 32 or the solid material 24 be other than water or stainless steel, respectively, it is necessary to recalculate this angle 50 depending upon the variation of the speed of sound within the different material, thus maintaining the angle 38 at the preferred magnitude of approximately 20°.

One other feature of the preferred embodiment is not apparent by examination of the drawing figures and has to do with the intensity of the sound radiation at the focal point 36. It is a basic tenet of the science of acoustics that the position of the most intense sound energy is not located at a point immediately adjacent a sound generator, but in fact occurs at some distance spaced therefrom. The distance to this point of maximum sound intensity, termed the Fresnel distance, is a function of the diameter of the sound generator and the wavelength of the sound being generated. The distance is defined by the following equation: Fresnel Distance $= 4D/\lambda$, where D equals the diameter of the sound generator and $\lambda$ equals the wavelength of the generated sound.

By locating the focal point 32 at the Fresnel distance from the transmitter 10, the intensity of the sound wave within the zone of interest is maximized, thereby increasing the effectiveness of the inspection. While the above equation is for sound waves traveling through only one medium, it is possible to extend the equation to cover sound traveling through a plurality of media, such as in the present invention. For this case, the Fresnel equation reduces to: $4D = L_1\lambda_1 + L_2\lambda_2$, wherein D equals the diameter of the sound generator, $L_1$ equals the distance traveled within the conductive medium (10a to 34), $\lambda_1$ equals the wavelength of the sound within the conductive medium 32, $L_2$ equals the distance traveled within the solid (34 to 36), and $\lambda_2$ equals the wavelength of the sound within the solid material 24. This equation will produce a line of solutions in $L_1$ and $L_2$ for given values of D, $\lambda_1$, and $\lambda_2$.

By fixing the focal point 36 a preselected distance 40 beneath the surface 22 of the solid material 24, the distance $L_2$ may be calculated based on a simple trigonometric relationship. This gives a unique solution to the above equation and determines the distance 51 above the surface 22 at which the carrier 18 must maintain the transmitter 10. For a stainless steel cladding ⅜ inch (1.0 cm) in thickness and immersed in water, the distance 51 would be approximately 3 inches (7.1 cm) above the surface 22. This would result in the focal point 36 being located both at a depth 40 of ⅜ inch below the surface 22 as well as at the Fresnel Distance from the sound transmitter.

Figure 3:
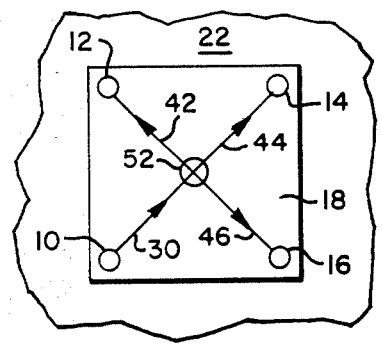
FIG. 3 shows the transmitted and reflected ultrasonic sound beams as viewed in the plane of the surface.

FIG. 3 shows a view of the transmitter 10 and receivers 12, 14, 16 as they would appear when viewed in a plane parallel to the plane of the surface 22. Also shown are representations of the pathways of the transmitted 30 and reflected 42, 44, 46 sound. The carrier 18 is also shown for reference. As can be seen from this view in FIG. 3, the transmitted sound beam 30 encounters the zone of interest 52 wherein it may be reflected in a variety of directions. The sound paths 42 and 46 will encounter the receivers 12, 16 of the preferred embodiment and will serve to detect cracks which may be present within the zone of interest as will be described more fully below. The receiver 14 is disclosed herein as part of an alternative embodiment for detecting those sound waves 44 which would be reflected back toward the surface 22 from the zone of interest 52 without a substantial change in direction when viewed in the plane of the surface 22 as shown in FIG. 3.

FIGS. 4a, b, and c show the ability of the present invention to differentiate between the various types of flaws which may be expected when examining a solid body, particularly a large cylindrical pressure vessel having an internal cladding 24 on a substrate 26.

FIG. 4a shows the reflection of the transmitted sound beam 30 upon encountering a longitudinal crack 54 present beneath the surface of a cylindrical vessel designated 22a. For detecting this type of defect, the transmitter 10 and the first receiver 12 are oriented so as to define a line 56 which is parallel to the longitudinal axis (not shown) of the cylindrical surface 22a. The transmitted sound beam 30 encounters the crack 54 at a 45° angle and is reflected therefrom on pathway 42. The reflected sound wave 42 is detected by receiver 12 but not by receivers 14 and 16 thus establishing the existence of both the defect 54 and its nature as a longitudinal crack.

FIG. 4b shows the detection of a circumferential crack 58 beneath the cylindrical surface 22a. The reflected sound wave 46 is seen as being detected by receiver 16 and no other thus indicating both the existence of the defect 58 and its nature as a circumferential crack. The receivers are oriented in 4b as in FIG. 4a with receivers 10 and 12 defining a line parallel to the longitudinal axis of the cylindrical surface 22a.

FIG. 4c shows the alternative embodiment according to the present invention being used to detect a delamination 60 present between the cladding 24 and the substrate 26 beneath the surface 22a. The sound 44 is reflected upward from the delamination 60 which acts as a mirror parallel to the surface 22a causing the transmitted sound beam 30 to be reflected upward without changing direction when viewed in the plane of the surface 22a. The detection of the sound wave 44 by the receiver 14 and no other indicates both the existence of the flaw 60 and the nature of the flaw as a delamination. Such flaws of delamination are relatively rare in nuclear pressure vessels, resulting in the embodiment of FIG. 4c being termed herein as an alternative rather than the preferred embodiment.

It should also be noted that, although the apparatus according to the present invention has been defined in terms of the plane of the surface 22, this is meant to include all substantially planar surfaces such as the cylindrical interior 22a of a nuclear pressure vessel or the like. These vessels are so large in comparison to the size of the apparatus that the inner surface 22a may be taken to be planar for all practical purposes. Should the surface of the solid body to be inspected be of a more pronounced curvature, it would be necessary to alter the orientation of the transmitter 10 and receivers 12, 14, 16 so as to result in the proper transmission and detection of the sound waves as disclosed herein.

The ultrasonic scanning system according to the present invention thus need only scan a particular point once to determine if a flaw exists within the zone of interest 52 located at a preselected distance 40 beneath the surface 22. This provides a considerable advantage over prior art systems wherein the ultrasonic scanning system must be passed over each individual point a plurality of times at a different orientation in order to ascertain: (1) if a flaw exists; (2) what is the nature of the flaw (circumferential crack, delamination, etc.); and (3) if the flaw is located at the interface between the cladding 24 and the substrate 26. By eliminating multiple scans, the apparatus the method according to the present invention results in significant savings of time and money during the service of nuclear power vessels.

We claim:

1. An ultrasonic inspection system for detecting the presence of flaws in a zone of interest surrounding a focal point disposed a preselected distance beneath a substantially planar surface of a solid material, said solid material being immersed in a sonic conducting medium, comprising:

a carrier for transporting said inspection system over the surface while maintaining a constant, fixed spacing therebetween;

an ultrasonic transmitter, secured to said carrier, for directing a beam of ultrasonic sound radiation through said medium and into said solid material toward said zone of interest, said transmitter further being oriented with respect to the surface so as to result in the formation of an included angle of approximately 20° between the beam path traveling within said material and said planar surface;

a first ultrasonic receiver, secured to said carrier, for receiving reflected ultrasonic sound originating as a result of the presence of a flaw within said zone of interest, said first receiver being oriented with respect to the surface of said material so as to receive only reflected sound originating within said zone of interest and traveling through said solid material along a reflected sound path forming an included angle of approximately 20° with said planar surface; and a second ultrasonic receiver, secured to said carrier, for receiving reflected ultrasonic sound originating as a result of the presence of a flaw within said zone of interest, said second receiver being oriented with respect to said planar surface of said material so as to receive only reflected sound originating within said zone of interest and traveling through said material along a reflected sound path forming an included angle of approximately 20° with said planar surface.

2. The inspection system as recited in claim 1, wherein the distance traveled by the transmitted sound beam between said transmitter and said zone of interest is equal to the Fresnel distance as determined for said transmitter and the sound wavelength when traveling through said medium and said solid material.

3. The inspection system as recited in claim 1, wherein:

said first receiver is further oriented for receiving only reflected sound traveling in a path perpendicular to the path of the transmitted sound beam when viewed in a plane parallel to said planar surface, and said second receiver is oriented for receiving only reflected sound traveling along a path perpendicular to the path of the transmitted sound beam when viewed in a plane parallel to said planar surface, said second receiver further being disposed opposite said first receiver with respect to said zone of interest.

4. The inspection system as recited in claim 3, wherein the distance traveled by said transmitted sound beam is equal to the Fresnel distance as determined by the diameter of said transmitter and the sound wavelength when traveling through said medium and said solid material.

5. The inspection system as recited in claim 3, further comprising a third ultrasonic receiver, secured to said carrier, for receiving reflected ultrasonic sound radiation originating as a result of the presence of a flaw within said zone of interest, said receiver being oriented with respect to said planar surface of said material for receiving only sound originating within said zone of interest and traveling through said material along a return path forming an included angle of approximately 20° with said planar surface, said third receiver further being oriented co-linearly with respect to said transmitter when viewed in a plane parallel to said planar surface.

6. The inspection system as recited in claim 5, wherein the distance traveled by said transmitted sound beam is equal to the Fresnel distance as determined by the diameter of said transmitter and the sound wavelength when traveling through said medium and said solid material.

7. A method for inspecting the surface of a generally cylindrical solid using the inspection system as recited in claim 3, comprising the steps of:

orienting the carrier with said transmitter and said first receiver defining a line parallel to the longitudinal axis of said cylindrical solid and positioning said carrier with respect to said cylindrical surface at said fixed distance; and traversing said surface of said cylindrical solid with the operating inspection system, whereby said first receiver receives reflected sound from any longitudinal cracks in said solid material within said zone of interest, and said second receiver receives reflected sound from any circumferential cracks present within said zone of interest in said solid material.

8. An ultrasonic inspection system for detecting the presence of flaws in a zone of interest beneath a substantially planar surface of a stainless steel body, said surface being immersed in water, comprising:
a carrier for traversing said surface while maintaining a fixed distance therebetween;
a transmitter, secured to said carrier for transmitting a beam of ultrasonic sound into said stainless steel, said transmitter oriented so as to result in the formation of an included angle of approximately 13.9° between the centerline of the transmitted beam and a line perpendicular to said planar surface within said water, said transmitter positioned so as to result in the passage of the transmitted beam through said zone of interest; and
a first receiver and a second receiver, each secured to said carrier in an opposing relationship, each spaced equidistant from said transmitter, and each oriented for receiving only sound reflected by flaws present within said zone of interest, said first and said second receiver further being oriented for receiving only sound traveling perpendicular to the transmitted beam when viewed in a plane parallel to said planar surface and having sound paths forming an included angle of approximately 13.9° between the path centerline within said water and a line perpendicular to said planar surface.

9. The inspection system as recited in claim 8, further comprising a third receiver, secured to said carrier and spaced equidistant from said first and said second receivers and oriented for receiving sound reflected only by flaws present within said zone of interest, said third receiver further being oriented for receiving sound traveling colinearly to the transmitted sound beam when viewed in a plane parallel to said planar surface and along a path within said water forming an included angle of approximately 13.9° with a line perpendicular to said planar surface.

10. The inspection system as recited in claim 8, wherein said fixed distance is equal to 3 inches, said zone of interest is $\frac{3}{8}$ of an inch beneath said planar surface of said stainless steel solid, said water immerses both said surface and said inspection system, and said transmitter generates sound with a frequency of 2.25 megahertz.

11. A method for ultrasonically inspecting a zone of interest located beneath a substantially planar surface of a solid material, comprising the steps of:
transmitting a beam of ultrasonic sound into said material and into said zone of interest, the centerline of said beam within said solid material forming an angle of about 20° with said planar surface; and
monitoring said surface of said solid material surrounding said zone of interest for detecting ultrasonic sound radiation being both reflected by a flaw present within said zone of interest and having a path centerline forming an included angle of approximately 20° with said planar surface within said solid material.

* * * * *

UNITED STATES PATENT AND TRADEMARK OFFICE
CERTIFICATE OF CORRECTION

PATENT NO. : 4,509,369
DATED : April 9, 1985
INVENTOR(S) : Zoran Kuljis, John P. Lareau, Mark V. Brook It is certified that error appears in the above—identified patent and that said Letters Patent is hereby corrected as shown below:

Title page, Item [75] Inventors: Add Mark V. Brook, West Hartford, Conn.

Column 3, line 39, change "(0.1 cm)" to --(1.0 cm)--.

Column 3, line 62, change "powder" to --power--.

Signed and Sealed this

Fifteenth Day of October 1985

[SEAL]

Attest:

*Attesting Officer*

DONALD J. QUIGG

*Commissioner of Patents and Trademarks—Designate*